(12) United States Patent
Shaligram

(10) Patent No.: US 11,857,178 B2
(45) Date of Patent: Jan. 2, 2024

(54) SURGICAL SUTURING INSTRUMENT

(71) Applicant: Abhijit Shaligram, Bangor, ME (US)

(72) Inventor: Abhijit Shaligram, Bangor, ME (US)

(*) Notice: Subject to any disclaimer, the term of this patent is extended or adjusted under 35 U.S.C. 154(b) by 403 days.

(21) Appl. No.: 17/094,626

(22) Filed: Nov. 10, 2020

(65) Prior Publication Data

US 2021/0137518 A1 May 13, 2021

Related U.S. Application Data

(60) Provisional application No. 62/934,989, filed on Nov. 13, 2019.

(51) Int. Cl.
*A61B 17/04* (2006.01)

(52) U.S. Cl.
CPC ...... *A61B 17/0483* (2013.01); *A61B 17/0467* (2013.01)

(58) Field of Classification Search
CPC ............ A61B 17/0467; A61B 17/0483; A61B 17/0487; A61B 17/08; A61B 17/083; A61B 17/122; A61B 2017/0488; A61B 2017/086

See application file for complete search history.

(56) References Cited

U.S. PATENT DOCUMENTS

| | | | |
|---|---|---|---|
| 1,822,330 A | 9/1931 | George | |
| 3,033,204 A | 5/1962 | Wood | |
| 3,090,386 A | 5/1963 | William | |
| 8,932,208 B2 | 1/2015 | Kendale et al. | |
| 2005/0143774 A1 | 6/2005 | Polo | |
| 2006/0200198 A1* | 9/2006 | Riskin | A61B 17/10 606/215 |
| 2017/0296163 A1* | 10/2017 | Levin | A61B 17/0401 |

* cited by examiner

*Primary Examiner* — Erich G Herbermann
*Assistant Examiner* — Mohammed S Adam

(57) ABSTRACT

The present invention is a surgical suturing device that assists in applying an open-looped, pre-knotted suture around a targeted area of application. The surgical suturing device contains a handle, a grasping mechanism, a first jaw, a second jaw, a first coupler, and a second coupler. The first jaw and the second jaw each contains a jaw body and a coupler receiver. The first coupler and the second coupler each contains a strand receiver. The handle is operatively connected to the first jaw and the second jaw through the grasping mechanism. The coupler receiver is positioned adjacent to the jaw body, opposite to the grasping mechanism along the jaw body. The first coupler is removably positioned within the coupler receiver of the first jaw. The strand receiver traverses into the first coupler and the second coupler. The second coupler is removably positioned within the coupler receiver of the second jaw.

7 Claims, 6 Drawing Sheets

SURGICAL SUTURING INSTRUMENT

The current application claims a priority to the U.S. Provisional Patent application Ser. No. 62/934,989 filed on Nov. 13, 2019.

FIELD OF THE INVENTION

The present invention relates generally to surgical suturing instrument. More specifically, the present invention is a surgical suturing instrument that allows a user to place an open-loop, pre-knotted suture over a targeted area of application without having to release hold over the targeted area of application.

BACKGROUND OF THE INVENTION

Currently, present society have enhanced current means of suturing during surgical procedures. In particular, traditional surgery can often involve looping a suture around a tissue and tying it off with knots. Clips can commonly be used to perform such function; however, they are mostly inflexible and inapplicable to most tissue types. Instead, pre-knotted sutures with a closed loop, known in the field as endoloops, can be favorable those applications unfulfilled by clips. However, these endoloops do present some challenges. For instance, in order to apply the endoloop to a target area of application, the user might have release and re-grasp their hold of the targeted area of application as they are trying to get the endoloop over or around the targeted area of application; sometimes repeatedly, which can unfavorable when dealing with certain targeted areas of application such as a bleeding vessel.

An objective of the present invention is to provide users with a device that is a surgical suturing instrument. The present invention intends to provide users with a device that can assist in applying an open-looped, pre-knotted suture around a targeted area of application, without the user having to release and re-grasp their hold on the targeted area of application repeatedly. The present invention intends to provide users with a device that utilizes an open-looped, pre-knotted suture that can be closed around a targeted area of application. The present invention intends to provide users with a device that can allow passage for said suture through to the front end of said device in which said suture is applied around targeted area of application. The present invention intends to provide users with a device that can grasp the free ends of said suture in order to form a closed loop around the targeted area of application. The present invention intends to provide users with a device that can allow passage of the knot of said suture through front tip of said device in order to close-off/tie-off said suture around targeted area of application.

SUMMARY OF THE INVENTION

The present invention is a surgical suturing device. The surgical suturing device comprises a handle, a grasping mechanism, a first jaw, a second jaw, a first coupler, and a second coupler. The first jaw and the second jaw each comprises a jaw body and a coupler receiver. The first coupler and the second coupler each comprises a strand receiver. The handle is operatively connected to the first jaw and the second jaw through the grasping mechanism. The coupler receiver is positioned adjacent to the jaw body, opposite to the grasping mechanism along the jaw body for each of the first jaw and the second jaw. In the preferred embodiment of the present invention, the coupler receiver mounts the first coupler and the second coupler to the first jaw and the second jaw. The first coupler is removably positioned within the coupler receiver of the first jaw. The strand receiver traverses into the first coupler and the second coupler. The second coupler is removably positioned within the coupler receiver of the second jaw.

DETAIL DESCRIPTIONS OF THE INVENTION

Figure 1:
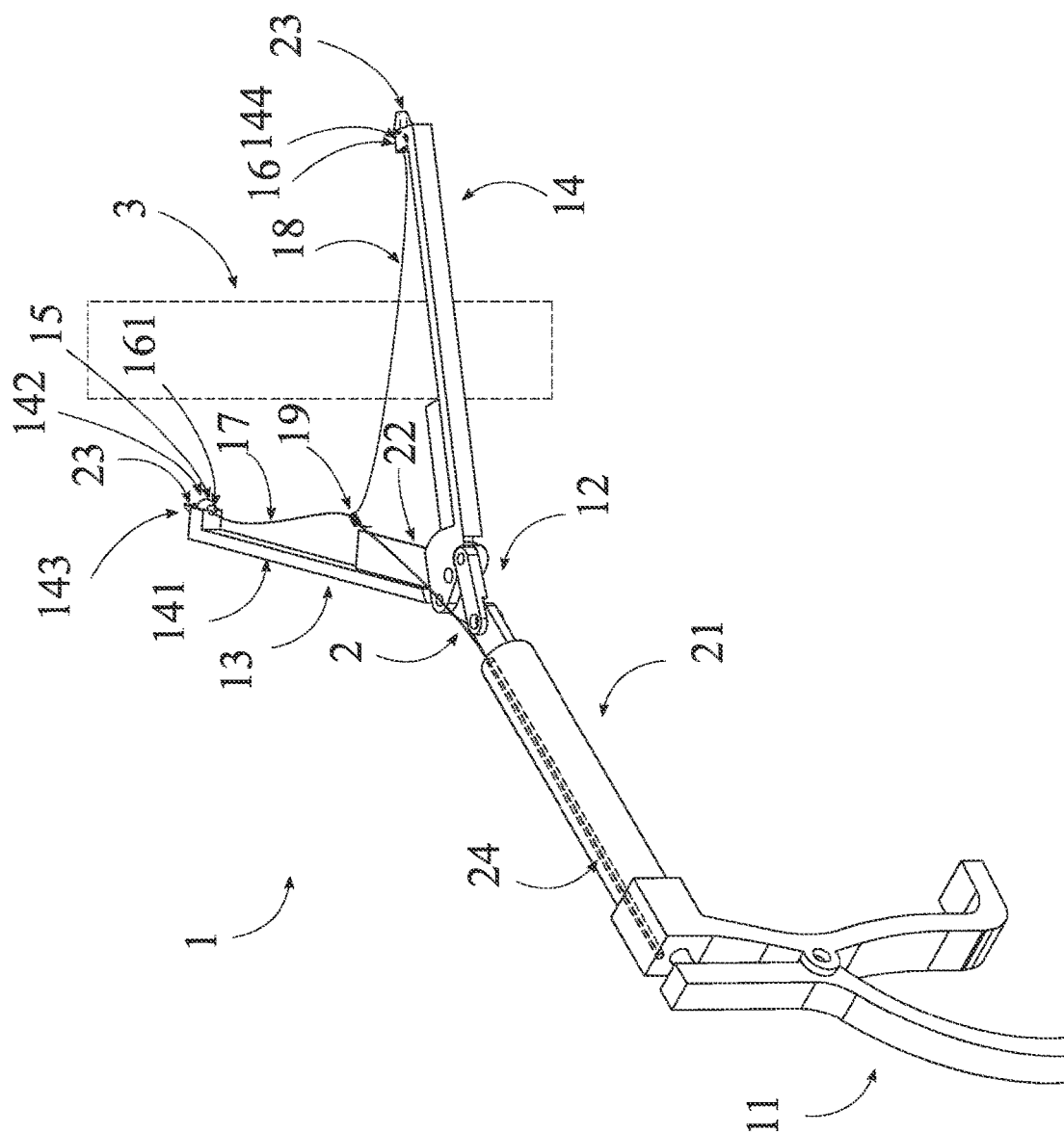
FIG. 1 is a perspective view of the present invention opened with an open loop.

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

In reference to FIGS. 1-6, the present invention is a surgical suturing device 1. The present invention can be of any shape, size, material, features, type or kind, orientation, location, quantity, components, and arrangements of components that would allow the present invention to fulfill the objectives and intents of the present invention. However, it can be preferred that the present invention be of a material that is sterile, hygienic, strong, durable, tough, light weight, easily cleanable, and/or easily manufacturable. The surgical suturing device 1 comprises a handle 11, a grasping mechanism 12, a first jaw 13, a second jaw 14, a first coupler 15, and a second coupler 16. The first jaw 13 and the second jaw 14 each comprises a jaw body 141 and a coupler receiver 142. The first coupler 15 and the second coupler 16 each comprises a strand receiver 161. The handle 11 is operatively connected to the first jaw 13 and the second jaw 14 through the grasping mechanism 12. The handle 11 can be of any shape, size, material, features, type or kind, orientation, location, quantity, components, and arrangements of components that would allow the present invention to fulfill the objectives and intents of the present invention. However, it can be preferred that the handle 11 assembly be of a material similar to and/or compatible with the material of the present invention. It can be preferred that the handle 11 assembly be of a general size that can accommodate the general sizes of an average user's hand. It can be preferred that the handle 11 be of a type or kind, shape, size, features, and/or components similar to handles commonly used or found on surgical devices. This can include, but is not limited to, the following: handles commonly found on laparoscopic suturing devices, laparoscopic grasper, ratcheting handle, or any other similarly related or similarly styled handle 11.

Figure 3:
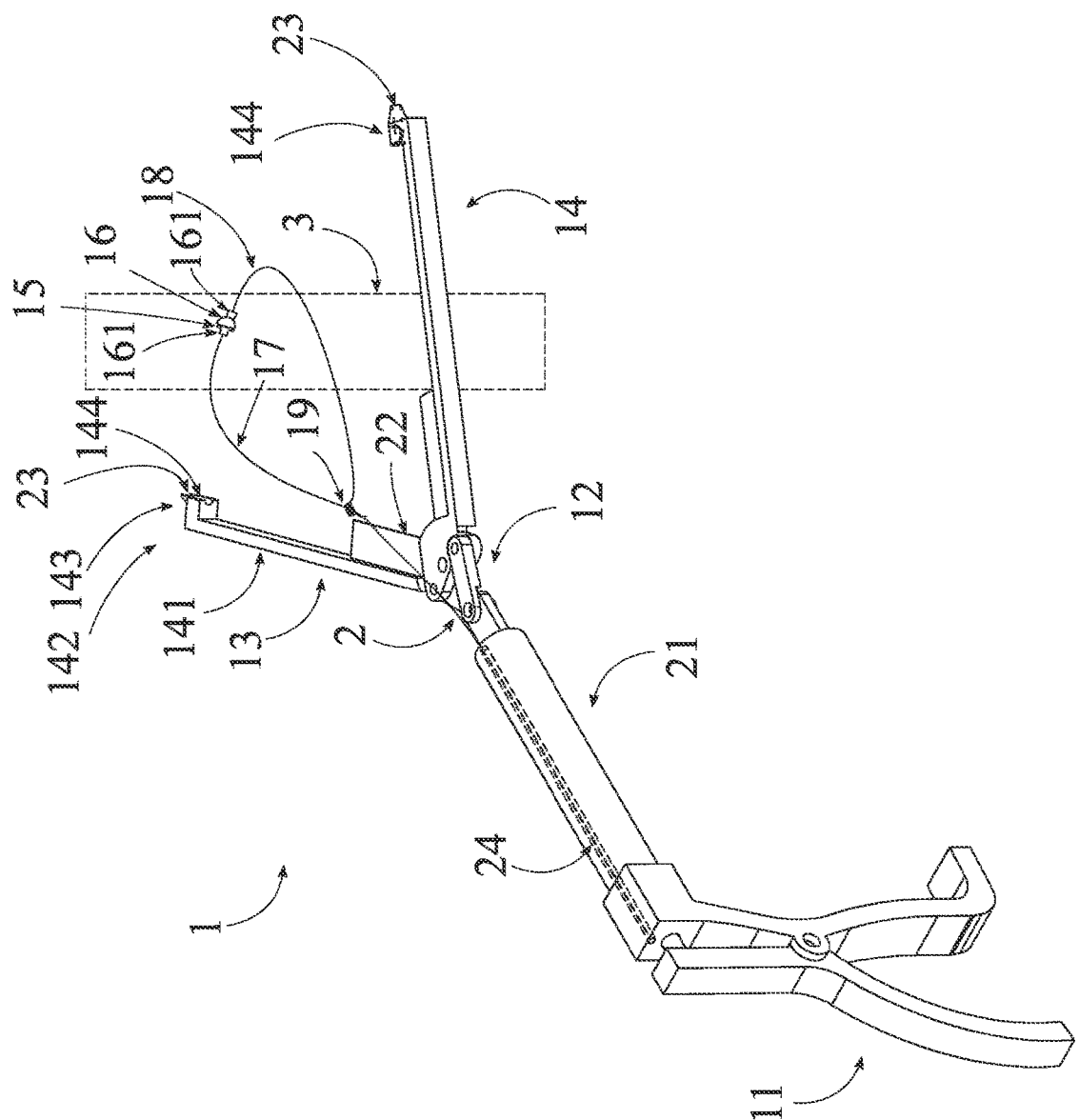
FIG. 3 is a perspective view of the present invention opened with the closed loop wrapped around a suturing portion.
Figure 5:
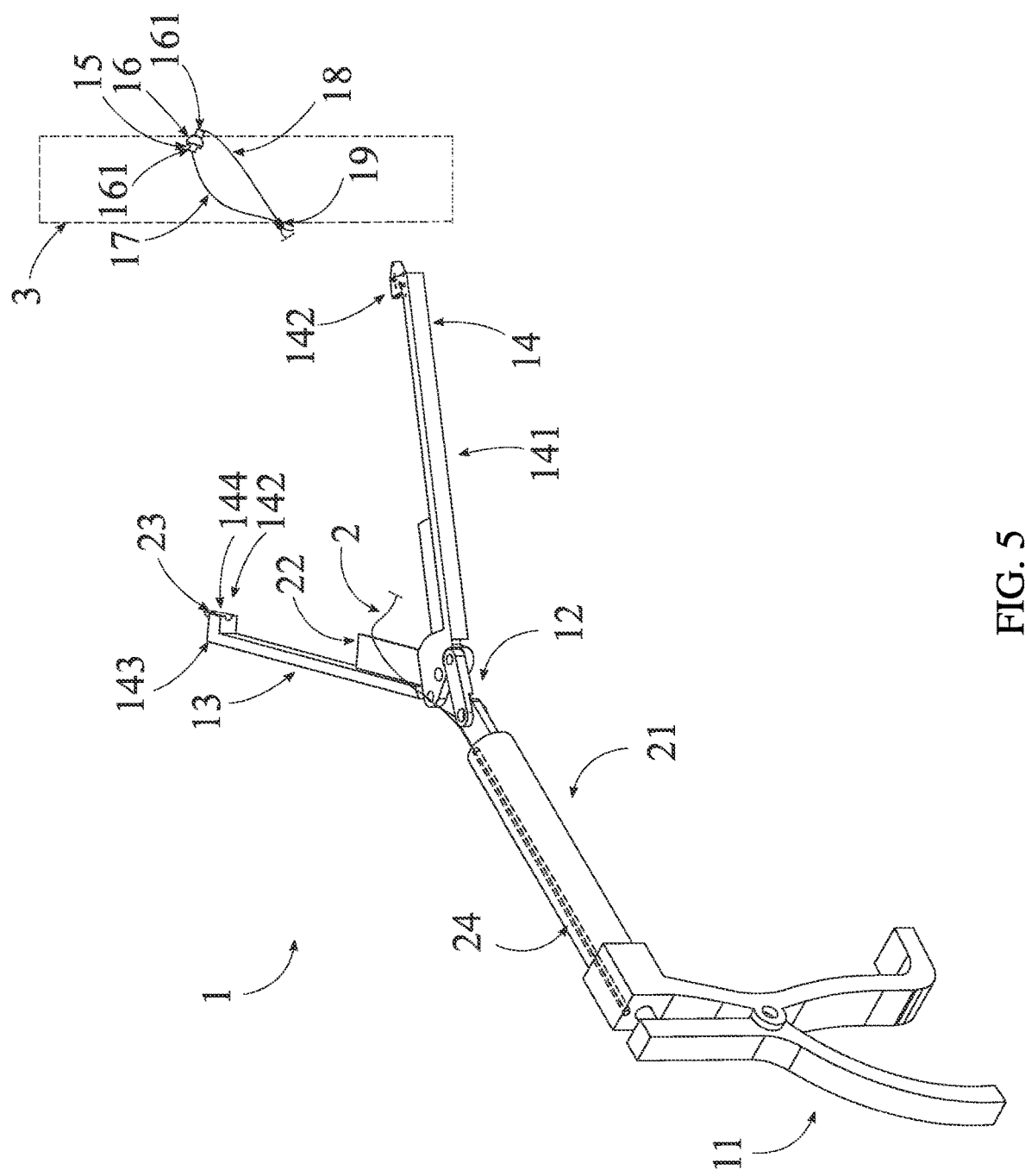
FIG. 5 is a perspective view of the present invention opened with a suture cord being cut along the tightened closed loop.

In reference to FIGS. 1, 3, and 5, the coupler receiver 142 is positioned adjacent to the jaw body 141, opposite to the grasping mechanism 12 along the jaw body 141 for each of the first jaw 13 and the second jaw 14. In the preferred embodiment of the present invention, the coupler receiver 142 mounts the first coupler 15 and the second coupler 16 to the first jaw 13 and the second jaw 14. The first coupler 15 is removably positioned within the coupler receiver 142 of the first jaw 13. The strand receiver 161 traverses into the first coupler 15 and the second coupler 16. The second coupler 16 is removably positioned within the coupler receiver 142 of the second jaw 14.

Figure 2:
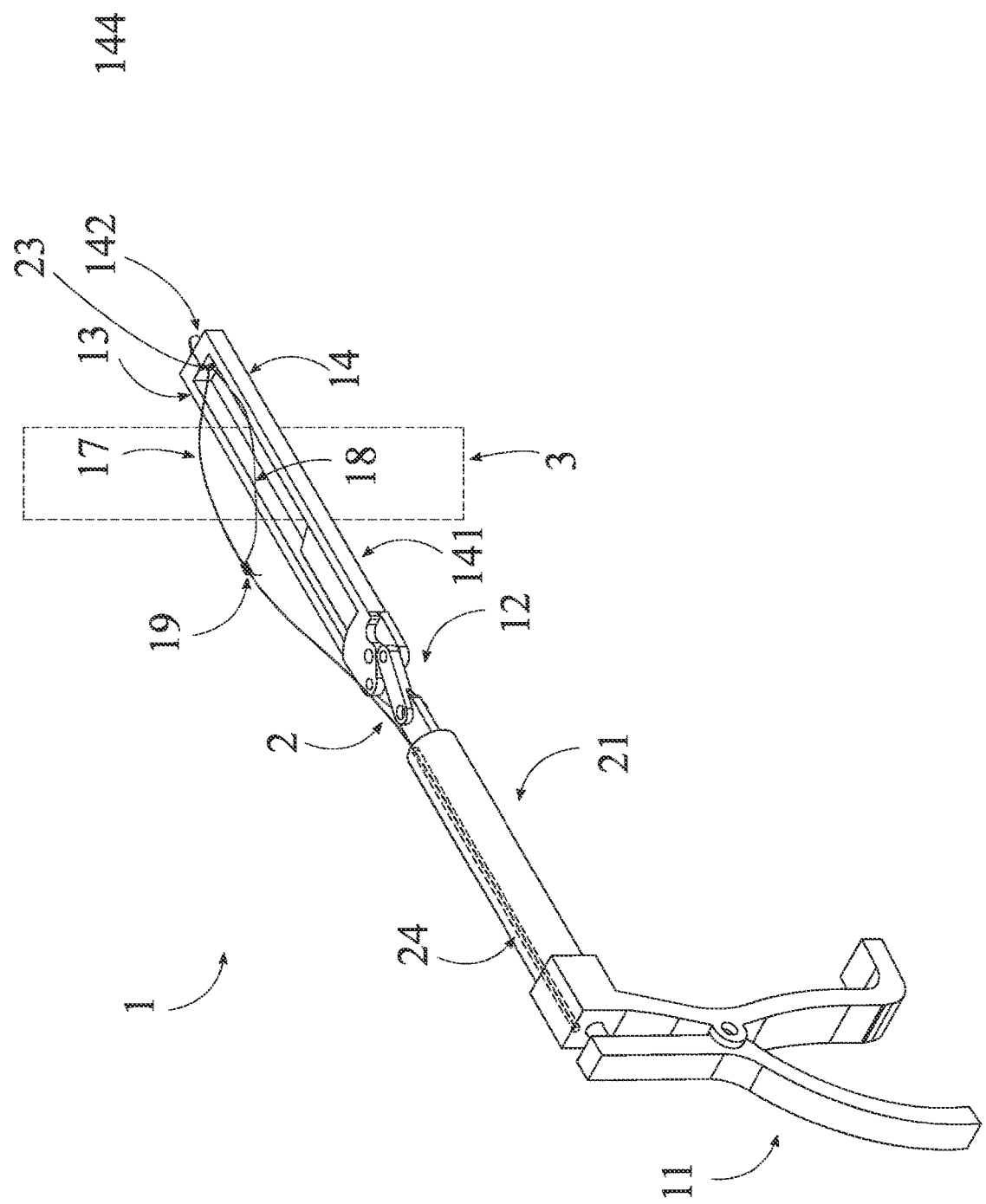
FIG. 2 is a perspective view of the present invention closed with a closed loop.

The surgical suturing device 1 further comprises a first strand 17 and a second strand 18. The first strand 17 is connected to the strand receiver 161 of the first coupler 15. The second strand 18 is connected to the strand receiver 161 of the second coupler 16. The first strand 17 serves as one segment of a suture cord 2 that will form the loop in conjunction with the second strand 18 which serves as the other segment of the suture cord 2. The surgical suturing device 1 further comprises an adjustment element 19. The adjustment element 19 is operatively connected to the first strand 17 and the second strand 18. In the preferred embodiment of the present invention, the adjustment element 19 may take the form of any suitable adjustment element 19 such as, but not limited to suture knots, clips, or any other suitable adjustment element 19 used to tighten the formed loop along a suturing portion 3. In the preferred embodiment of the present invention, the first coupler 15 and the second coupler 16 conjoin the first strand 17 and the second strand 18 together, while disengaging along the jaw body 141, forming a completed suture loop, as shown in FIGS. 2 and 3.

The surgical suturing device 1 further comprises a shaft 21, as shown in FIGS. 1-6. The handle 11 is connected adjacent to the shaft 21. The grasping mechanism 12 traverses along the shaft 21 between the handle 11 and the first jaw 13 and the second jaw 14. The shaft 21 can be of any shape, size, material, features, type or kind, orientation, location, quantity, components, and arrangements of components that would allow the present invention to fulfill the objectives and intents of the present invention. However, it can be preferred that the shaft 21 be of a material similar to and/or compatible with the material of the handle 11. It can be preferred that the shaft 21 be of a shape similar to a cylindrical-like shaped figure. It can be preferred that the shaft 21 be located at the front face of the handle 11 assembly and near to the top face of the handle 11 assembly.

Figure 4:
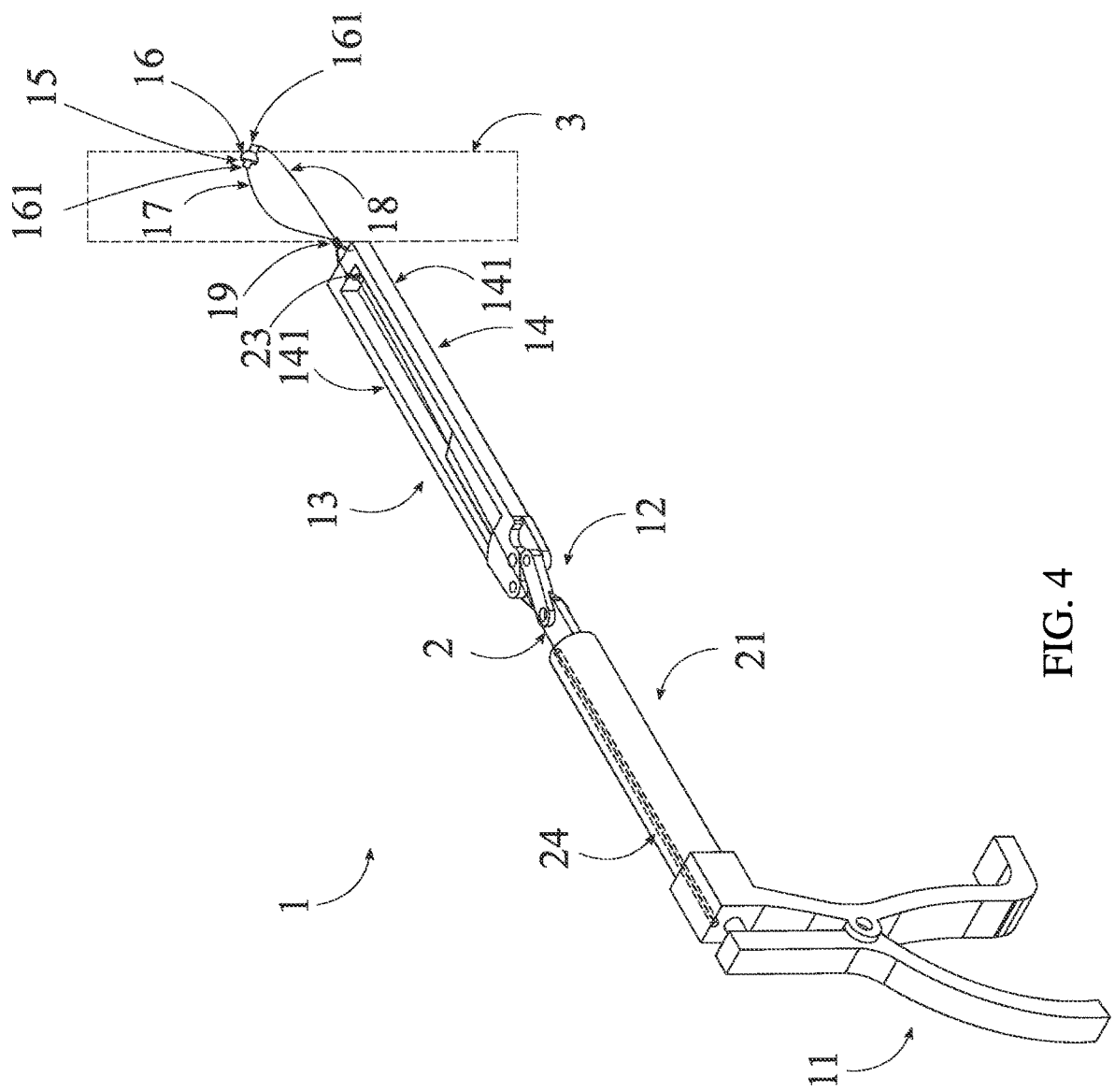
FIG. 4 is a perspective view of the present invention closed with the closed loop being tightened along the suturing positioned.

The surgical suturing device 1 further comprises a cutter 22, as shown in FIGS. 1, 3, and 5. The cutter 22 is positioned adjacent to the jaw body 141 of the first jaw 13 and the second jaw 14, opposite to the strand receiver 161. The cutter 22 can be of any shape, size, material, features, type or kind, orientation, location, quantity, components, and arrangements of components that would allow the present invention to fulfill the objectives and intents of the present invention. The cutter 22 allows the user to cut the excess suture cord 2 once the suture has been applied to the suturing area, as shown in FIG. 5. The surgical suturing device 1 further comprises a strand aperture 23, as shown in FIGS. 1-5. The strand aperture 23 traverses through the coupler receiver 142. The strand aperture 23 allows the user to handle 11 the suture cord 2 when tightening the loop along the suturing portion 3, as shown in FIG. 4.

Figure 6:
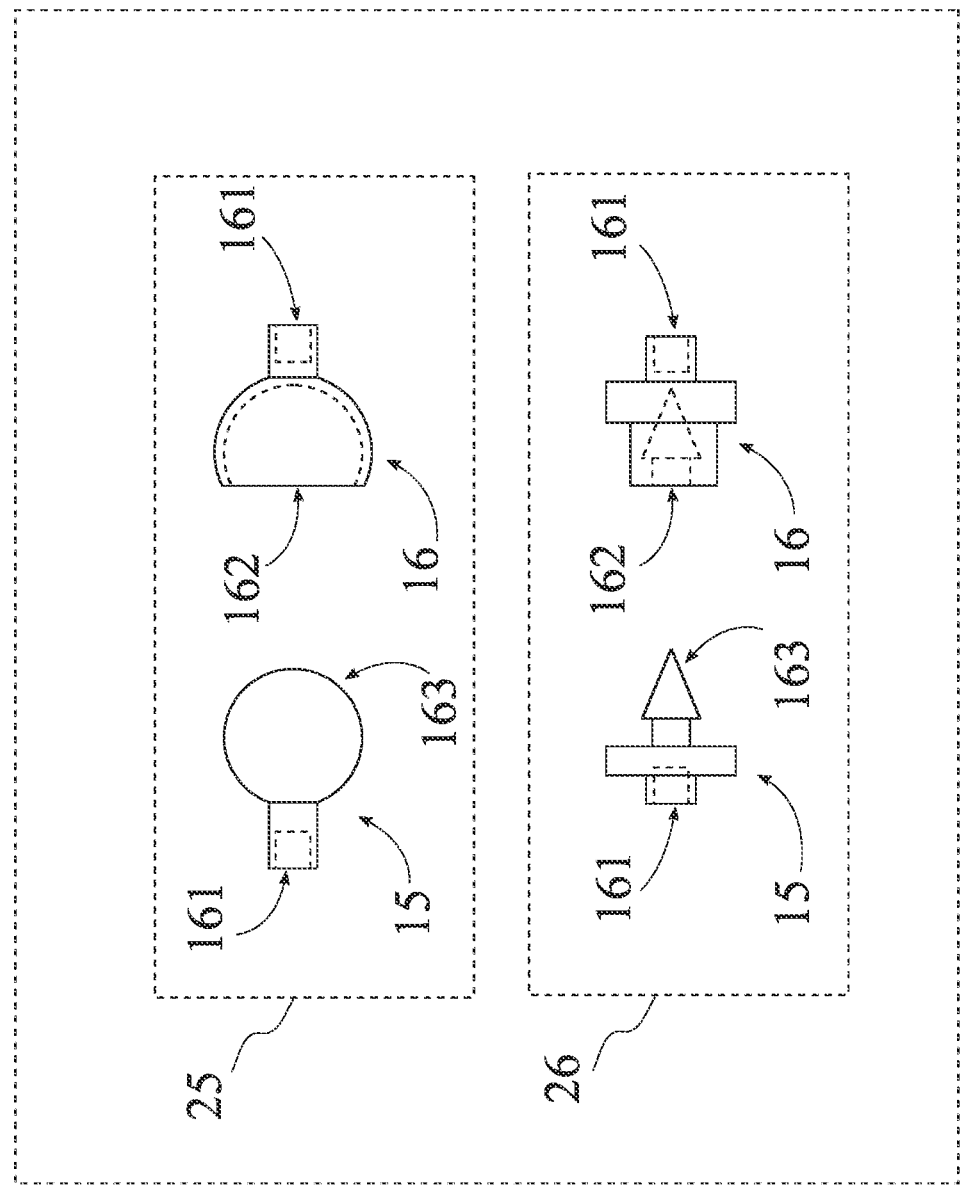
FIG. 6 is a diagram view of a ball and socket coupler and a snap rivet coupler.

The coupler receiver 142 comprises a receiver body 143 and a receiver cavity 144, as shown in FIGS. 1, 3, and 5. The receiver body 143 is connected adjacent to the jaw body 141. The receiver cavity 144 traverses into the receiver body 143. The strand aperture 23 traverses through the receiver body 143. In the preferred embodiment of the present invention, the receiver body 143, in conjunction with the receiver cavity 144, mounts the first coupler 15 and the second coupler 16 along the first jaw 13 and the second jaw 14 of the surgical suturing device 1. In the preferred embodiment of the present invention, the first coupler 15 and the second coupler 16 each is a snap-rivet coupler 26, as shown in FIG. 6. In the preferred embodiment of the present invention, the first coupler 15 and the second coupler 16 each is a ball and socket coupler 25, as shown in FIG. 6. In various embodiments of the present invention, the first coupler 15 and the second coupler 16 may take the form of any other suitable type of coupling implement, such as, but not limited to barb connectors, tabs, adhesives, welding agents, or any other suitable coupling implement. In reference to FIG. 6, the first coupler comprises a coupler fastener 163. The second coupler comprises a coupler cavity 162. The coupler fastener 163 is positioned adjacent to the strand receiver of the first coupler. The coupler cavity 162 is positioned adjacent to the strand receiver of the second coupler. The coupler fastener 163 is connected to the coupler cavity 162 when the coupler fastener 163 of the first coupler and the coupler cavity 162 of the second coupler are pressed together when the first jaw and the second jaw are in a closed configuration. The coupler fastener 163 serves as the male connection implement of the first coupler and the coupler cavity 162 serves as the female connection implement of the second coupler.

In the preferred embodiment of the present invention, the surgical suturing device 1 comprises a suture channel 24, as shown in FIGS. 1-5. The suture channel 24 traverses through the shaft 21. The suture channel 24 allows the user to replace the spent suture cord 2 with a pre-knotted suture along the shaft 21 portion of the surgical suturing device 1 ready for the next suture operation.

Although the invention has been explained in relation to its preferred embodiment, it is to be understood that many other possible modifications and variations can be made without departing from the spirit and scope of the invention as hereinafter claimed.

What is claimed is:

1. A surgical suturing device comprising:
   a handle;
   a grasping mechanism;
   a first jaw;
   a second jaw;
   a first coupler;
   a second coupler;
   a first strand;
   a second strand;
   a shaft;
   a cutter;
   the first jaw and the second jaw each comprising a jaw body and a coupler receiver;
   the first coupler and the second coupler each comprising a strand receiver;

the handle being operatively connected to the first jaw and the second jaw through the grasping mechanism;

the coupler receiver being positioned adjacent to the jaw body, opposite to the grasping mechanism along the jaw body for each of the first jaw and the second jaw;

the first coupler being removably positioned within the coupler receiver of the first jaw;

each of the strand receiver traversing into the first coupler and the second coupler, respectively;

the second coupler being removably positioned within the coupler receiver of the second jaw;

the first strand being connected to the strand receiver of the first coupler;

the second strand being connected to the strand receiver of the second coupler;

the handle being connected adjacent to the shaft;

the grasping mechanism traversing along the shaft between the handle and the first jaw and the second jaw;

the cutter being positioned adjacent to the jaw body of the first jaw and the second jaw;

the cutter being positioned opposite to the strand receiver of the first coupler and the second coupler;

the first coupler comprising a coupler fastener;

the second coupler comprising a coupler cavity;

the coupler fastener being positioned adjacent to the strand receiver of the first coupler;

the coupler cavity being positioned adjacent to the strand receiver of the second coupler; and the coupler fastener being connected to the coupler cavity, wherein the coupler fastener of the first coupler and the coupler cavity of the second coupler are pressed together when the first jaw and the second jaw are in a closed configuration.

2. The surgical suturing device as claimed in claim 1 comprising:

an adjustment element;

the adjustment element being operatively connected to the first strand and the second strand; and the adjustment element being in a form of a suture knot.

3. The surgical suturing device as claimed in claim 1 comprising:

a strand aperture; and the strand aperture traversing through the coupler receiver of the first jaw and the coupler receiver of the second jaw.

4. The surgical suturing device as claimed in claim 1 comprising:

a strand aperture;

the coupler receiver of the first jaw comprising a receiver body and a receiver cavity;

the coupler receiver of the second jaw comprising a receiver body and a receiver cavity;

each of the receiver body being connected adjacent to the respective jaw body;

each of the receiver cavity traversing into the respective receiver body; and the strand aperture traversing through the receiver body of the first jaw and the receiver body of the second jaw.

5. The surgical suturing device as claimed in claim 1 comprising:

a suture channel; and the suture channel traversing through the shaft.

6. The surgical suturing device as claimed in claim 1, wherein the first coupler and the second coupler each being a part of a snap-rivet coupler.

7. The surgical suturing device as claimed in claim 1, wherein the first coupler and the second coupler each being a part of a socket coupler.

* * * * *